(12) United States Patent
Oishi

(10) Patent No.: US 10,420,461 B2
(45) Date of Patent: Sep. 24, 2019

(54) IMAGE GENERATING APPARATUS, IMAGE GENERATING METHOD, AND STORAGE MEDIUM

(71) Applicant: CANON KABUSHIKI KAISHA, Tokyo (JP)

(72) Inventor: Satoru Oishi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 87 days.

(21) Appl. No.: 15/139,084

(22) Filed: Apr. 26, 2016

(65) Prior Publication Data

US 2016/0317016 A1 Nov. 3, 2016

(30) Foreign Application Priority Data

May 1, 2015 (JP) .................. 2015-094342

(51) Int. Cl.
*A61B 3/00* (2006.01)
*A61B 3/14* (2006.01)
*A61B 3/10* (2006.01)

(52) U.S. Cl.
CPC .................. *A61B 3/102* (2013.01)

(58) Field of Classification Search
CPC . G06T 2207/10101; G06T 2207/30041; G06T 2207/30104; G06T 7/0016; G06T 7/11; G06T 15/08; G06T 2207/20044; G06T 2211/404; G06T 7/0012; G06T 7/0014; G06T 11/003; G06T 11/006; G06T 15/10; G06T 19/00; G06T 2207/10016; G06T 2207/10028; A61B 3/102; A61B 3/0025; A61B 3/1233; A61B 5/0066; A61B 5/0261; A61B 3/0058; A61B 3/0041; A61B 3/14; A61B 5/6821; A61B 2576/00; A61B 3/0091; A61B 3/1025; A61B 3/1241; A61B 3/145; A61B 5/1128; A61B 5/4836; A61B 5/489
(Continued)

(56) References Cited

U.S. PATENT DOCUMENTS

2014/0160487 A1 6/2014 Huang
2014/0221827 A1* 8/2014 Motaghiannezam ......... G01N 21/4795
600/425

(Continued)

FOREIGN PATENT DOCUMENTS

CN 101264023 A 9/2008
CN 104271031 A 1/2015
(Continued)

*Primary Examiner* — Brandi N Thomas
(74) *Attorney, Agent, or Firm* — Canon U.S.A., Inc. IP Division

(57) ABSTRACT

An image generating apparatus includes an obtaining unit configured to obtain plural pieces of tomographic image data, in which each piece of tomographic image data indicates a cross section of substantially the same position of a subject, a calculation unit configured to calculate a motion contrast value based on the plural pieces of tomographic image data and a comparison result of a representative value of the plural pieces of tomographic image data indicating a signal intensity and a threshold, a generation unit configured to generate a motion contrast image of the subject based on the motion contrast value, and a change unit configured to change the threshold.

18 Claims, 12 Drawing Sheets

(58) Field of Classification Search
USPC ........ 351/200, 205–206, 209–211, 221, 222, 351/243–246
See application file for complete search history.

(56) References Cited

U.S. PATENT DOCUMENTS

2014/0293222 A1    10/2014  Coelho
2015/0272434 A1*   10/2015  Satake ................. A61B 3/0058
                                                        351/206

FOREIGN PATENT DOCUMENTS

| | | |
|---|---|---|
| JP | 2011072446 A | 4/2011 |
| JP | 2012021794 A | 2/2012 |
| JP | 2015009108 A | 1/2015 |
| WO | 2013167641 A1 | 11/2013 |

* cited by examiner

FIG. 6
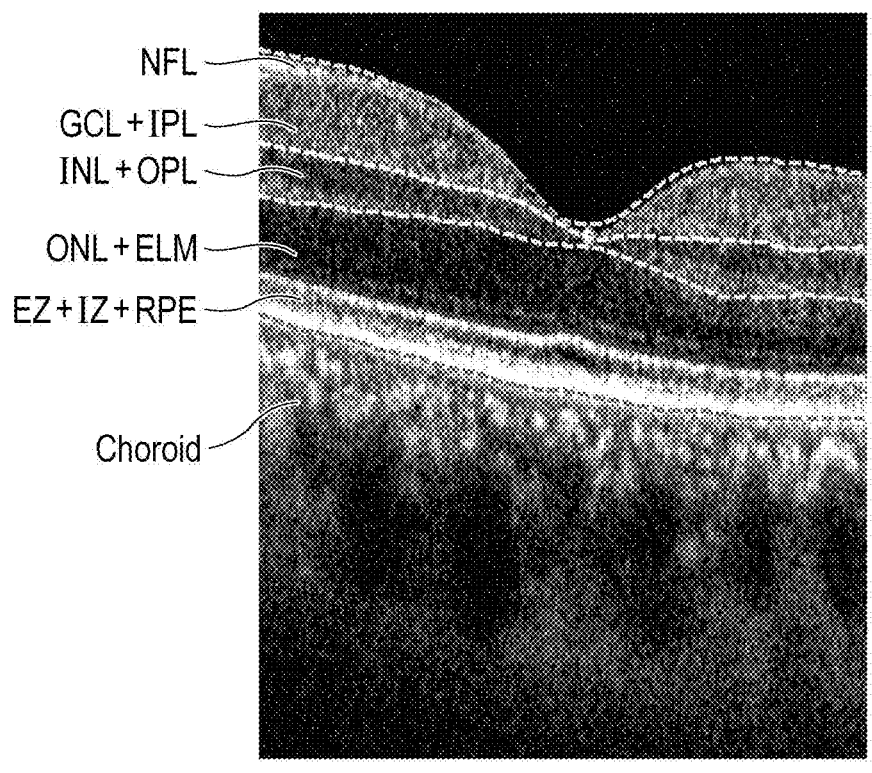
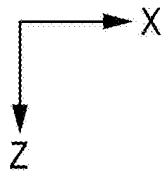

FIG. 7
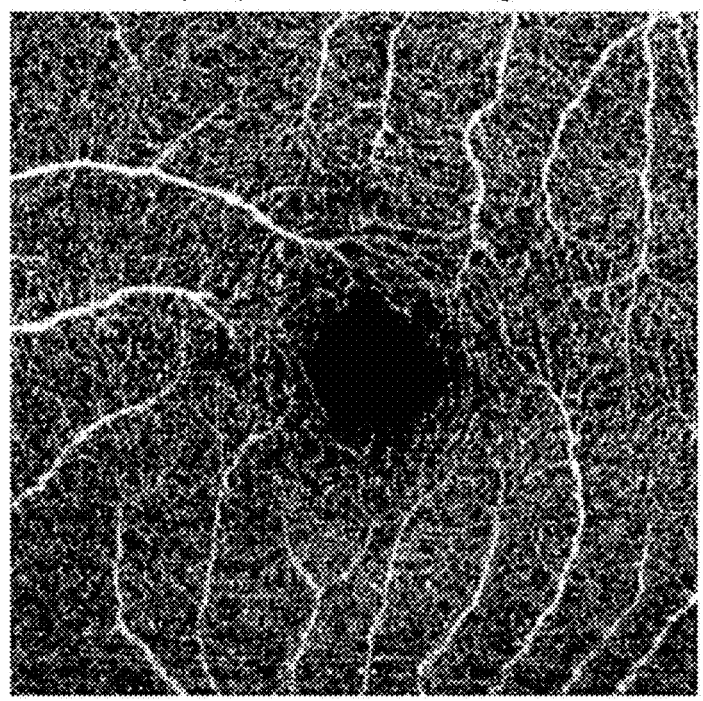
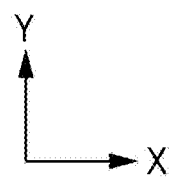

IMAGE GENERATING APPARATUS, IMAGE GENERATING METHOD, AND STORAGE MEDIUM

BACKGROUND

Field

A technology according to the disclosure relates to an image generating apparatus, an image generating method, and a storage medium.

Description of the Related Art

A tomographic image is an image of internal structures of a solid object (such as the human body or the earth) by observation and recording of differences in effects on passage of waves of energy impinging on those structures. Optical coherence tomography (OCT) is a noninvasive imaging test that uses light waves to take cross-section pictures of, for example, a retina, which is the light-sensitive tissue lining the back of an eye. As a method of obtaining a tomographic image of a measurement object such as a living matter in a nondestructive and noninvasive manner, an optical coherence tomography (hereinafter, will be referred to as OCT) has been put into practice. The OCT is widely used, particularly in an ophthalmic diagnosis relating to the eye and its diseases.

According to the OCT, a tomographic image of a measurement object is obtained while light reflected from the measurement object interferes with light reflected from a reference mirror, and an intensity of the interfering light is analyzed. Apparatuses that obtain the above-described optical coherence tomography have been proposed, including a time domain OCT apparatus configured to obtain depth information of the measurement object by changing a position of the reference mirror, a spectrum domain OCT (spectral domain optical coherence tomography: SD-OCT) apparatus configured to separate the interfering light and replace the depth information with frequency information to be obtained, and a wavelength-sweeping light coherence tomography (swept source optical coherence tomography: SS-OCT) apparatus configured to previously separate a wavelength to be output. It should be noted that the SD-OCT and the SS-OCT are also collectively called Fourier domain optical coherence tomography (FD-OCT).

Angiography, or arteriography, is a medical imaging technique used to visualize the inside, or lumen, of blood vessels and organs of the body, with particular interest in the arteries, veins, and the heart chambers. In recent years, a blood vessel radiographic contrasting method using FD-OCT has been proposed, and this blood vessel radiographic contrasting method is called OCT angiography. U.S. Patent Application Publication No. 2014/0221827 discloses an OCT angiography in which a variation of a logarithmic intensity of an interfering signal is set as a motion contrast feature quantity, and imaging of the motion contrast feature quantity is performed.

According to the method disclosed in U.S. Patent Application Publication No. 2014/0221827, while a value that is 10 decibel (dB) above a noise floor average value is set as a threshold, this threshold is compared with an intensity of the interfering signal, and the motion contrast feature quantity corresponding to the intensity of the interfering signal below the threshold is set as 0.

However, a signal intensity of noise or a signal intensity of the blood vessel varies in accordance with a position or a layer in a depth direction of the retina in a tomographic image obtained by an actual OCT. For this reason, in a case where the threshold is set as a fixed value as in U.S. Patent Application Publication No. 2014/0221827, there are probabilities that the noise is regarded as the blood vessel and the blood vessel is regarded as the noise depending on the position or the layer in the depth direction of the retina. That is, there are probabilities that imaging of the blood vessel is not carried out at a high accuracy according to the related art technology.

SUMMARY

The technology according to the disclosure has been made in view of the above-described issue and aims at carrying out the imaging of the blood vessel at a high accuracy.

It should be noted that, in addition to the above-described purpose, provision of effects and advantages, which are not attained by a related-art technology, derived from the respective configurations illustrated in the exemplary embodiments for carrying out the disclosed image generating apparatus, which will be described below, can be also regarded as one of the other purposes of the present disclosure.

An image generating apparatus according to an aspect of the disclosure includes an obtaining unit configured to obtain plural pieces of tomographic image data, in which each piece of tomographic image data indicates a cross section of substantially the same position of a subject; a calculation unit configured to calculate a motion contrast value based on the plural pieces of tomographic image data and a comparison result of a representative value of the plural pieces of tomographic image data indicating a signal intensity and a threshold; a generation unit configured to generate a motion contrast image of the subject based on the motion contrast value; and a change unit configured to change the threshold.

Further features of the present invention will become apparent from the following description of exemplary embodiments with reference to the attached drawings.

BRIEF DESCRIPTION OF THE DRAWINGS

FIG. 6 illustrates an example of a segmentation result.

FIG. 7 illustrates an example of an OCT angiography image according to the first exemplary embodiment.

DESCRIPTION OF THE EMBODIMENTS

Hereinafter, with reference to the accompanying drawings, an image forming apparatus according to an exemplary embodiment will be described. It should be noted that configurations illustrated in the following exemplary embodiments are merely examples, and the present disclosure is not limited to the following exemplary embodiments.

First Exemplary Embodiment

Configuration of an Entire Image Pickup Apparatus

Hereinafter, with reference to the drawings, an example of the present exemplary embodiment will be described.

Figure 1:
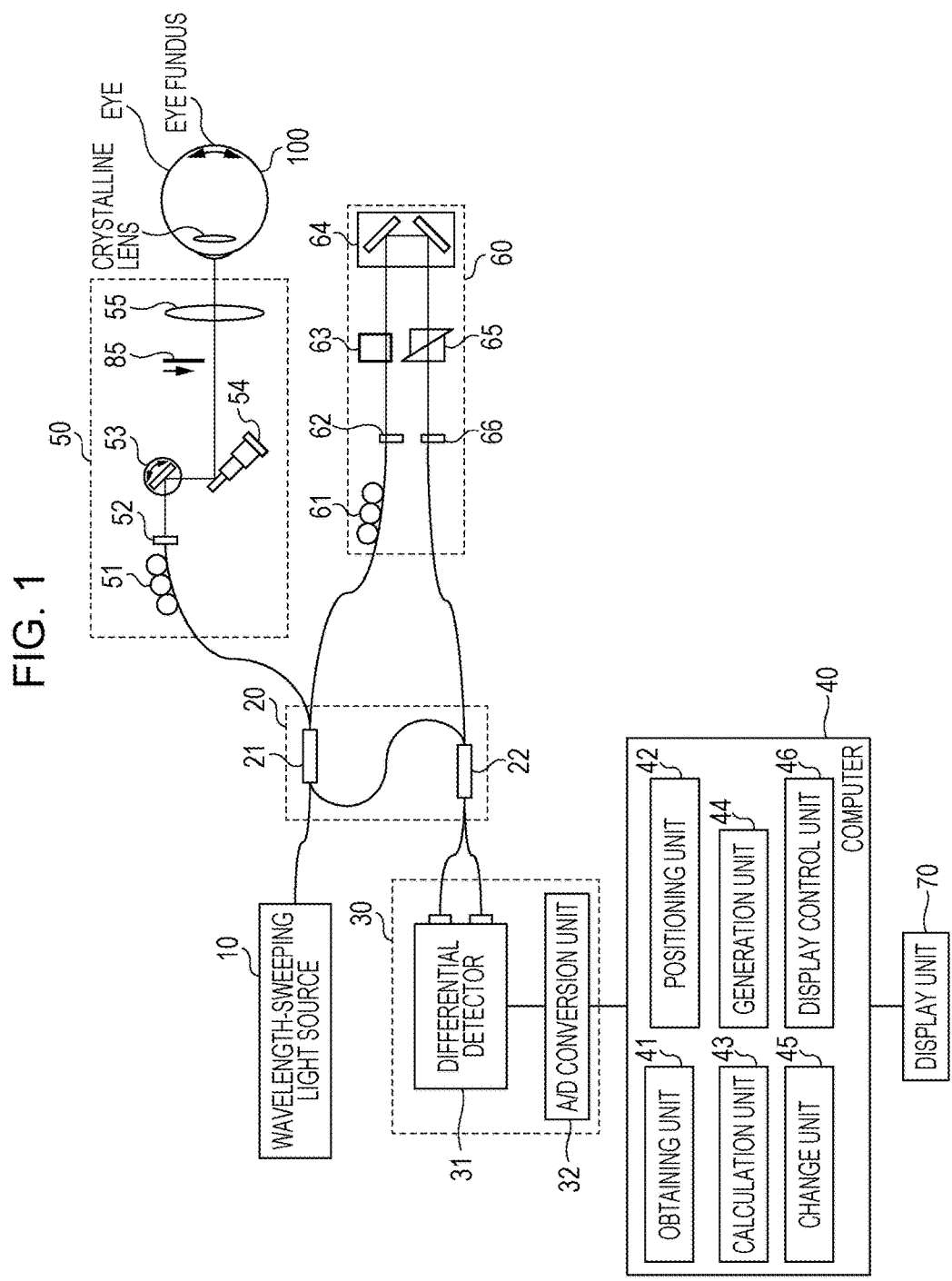
FIG. 1 illustrates an example of an overall configuration of an image pickup apparatus according to a first exemplary embodiment.

FIG. 1 illustrates a configuration example of an image pickup apparatus (OCT apparatus) using the optical coherence tomography according to the present exemplary embodiment. FIG. 1 illustrates the configuration in a case where the image pickup apparatus is an SS-OCT apparatus, but a similar effect can be realized by other OCT apparatuses using other methods.

The present OCT apparatus includes a wavelength-sweeping light source 10, an optical signal branching/multiplexing unit 20, a detection unit 30 for the interfering light, a computer 40 (image generating apparatus) configured to obtain retina information of a human eye 100, a measurement arm 50, and a reference arm 60. The computer 40 is provided with a central processing unit (CPU) and a storage device. The storage device is constituted, for example, by a memory (RAM and ROM) and a large capacity storage device (HDD). Part or an entirety of the storage device may be provided outside of the computer 40. The wavelength-sweeping light source 10 emits, for example, light having a wavelength of 980 nanometers (nm) to 1100 nm at a frequency of 100 kilohertz (kHz) (a scanning rate). Herein, the wavelength and the frequency are for illustrative purposes, and the present disclosure is not limited to the above-described values. Similarly, as in the following exemplary embodiments, the described numeric values are for illustrative purposes, and the present disclosure is limited to the described numeric values.

An eye fundus is the interior lining of an eyeball, including the retina (the light-sensitive screen), optic disc (the head of the nerve to the eye), and the macula (the small spot in the retina where vision is keenest). It should be noted that a subject is set as a human eye (eye fundus) 100 according to the present exemplary embodiment but is not limited to this. For example, the present exemplary embodiment may be used for a skin or the like. In addition, the eye fundus of the eye is set as an image pickup object according to the present exemplary embodiment, but an anterior segment of the eyeball, the front third of the eye that includes the structures in front of the vitreous humour: the cornea, iris, ciliary body, and lens, may be set as the image pickup object.

The optical signal branching/multiplexing unit 20 includes couplers 21 and 22. The coupler 21 first branches the light emitted from the wavelength-sweeping light source 10 into reference light and irradiation light with which the eye fundus of the human eye 100 is irradiated. The human eye 100 is irradiated with the irradiation light via the measurement arm 50. More specifically, after a polarization state of the irradiation light incident on the measurement arm 50 is rectified by a polarization controller 51, the irradiation light is emitted from a collimator 52 as spatial light. Thereafter, the eye fundus of the human eye 100 is irradiated with the irradiation light via an X-axis scanner 53, a Y-axis scanner 54, and a focus lens 55. It should be noted that the X-axis scanner 53 and the Y-axis scanner 54 are scanning units having a function of scanning the eye fundus by the irradiation light. The irradiation position of the eye fundus with the irradiation light can be changed by the scanning unit 53/54. Herein, obtaining of information in a perspective direction (depth direction) of one point of the human eye 100 is referred to as an A scanning. Obtaining of a two-dimensional tomographic image along a direction orthogonal to the A scanning is referred to as a B scanning. Obtaining of the two-dimensional tomographic image along a direction perpendicular to the two-dimensional tomographic image of the B scanning is referred to as a C scanning.

It should be noted that the X-axis scanner 53 and the Y-axis scanner 54 are constituted by mirrors arranged in a manner that respective rotation axes are orthogonal to each other. The X-axis scanner 53 performs scanning in an X-axis direction, and the Y-axis scanner 54 performs scanning in a Y-axis direction. The respective directions of the X-axis direction and the Y-axis direction are directions perpendicular to an eye axis of the eye ball 100 and are directions perpendicular to each other. A line scanning direction, such as the B scanning and the C scanning, may be matched or may not be matched with the X-axis direction or the Y-axis direction. For this reason, the line scanning direction of the B scanning and the C scanning can be appropriately determined in accordance with the two-dimensional tomographic image or the three-dimensional tomographic image desired to be picked up.

Reflected light from the eye fundus passes through the coupler 21 via the same route again such as the focus lens 55 to be incident on the coupler 22. It should be noted that, when measurement is performed while a shutter 85 is closed, it is possible to measure a background (noise floor) by cutting the reflected light from the human eye 100.

On the other hand, the reference light is incident on the coupler 22 via the reference arm 60. More specifically, after a polarization state of the reference light incident on the reference arm 60 is rectified by a polarization controller 61, the reference light is emitted from a collimator 62 as the spatial light. Thereafter, the reference light passes through a dispersion compensation glass 63, a light path length adjusting optical system 64, and a dispersion adjusting prism pair 65 to be incident on an optical fiber via a collimator 66 and is emitted from the reference arm 60 to be incident on the coupler 22.

In the coupler 22, the reflected light of the human eye 100 that has passed through the measurement arm 50 interferes the reference light with that has passed through the reference arm 60. Subsequently, the interfering light is detected by the detection unit 30. The detection unit 30 includes a differential detector 31 and an analog-to-digital (A/D) converter 32. First, in the detection unit 30, the interfering light separated by the coupler 22 is detected by the differential detector 31. Subsequently, an OCT interfering signal (hereinafter, may be referred to simply as an interfering signal in some cases) converted into an electric signal by the differential detector 31 is converted into a digital signal by the A/D converter 32. Herein, sampling of the interfering light by the differential detector 31 is performed by a weighted ordinate method based on k clock signals generated by a clock generator incorporated in the wavelength-sweeping light source 10. The digital signal output by the A/D converter 32 is transmitted to the computer 40. Next, the computer 40 performs signal processing on the interfering signal converted into the digital signal to calculate an OCT angiography image. An image illustrated in FIG. 7 is an example of the OCT angiography image.

The CPU provided to the computer 40 executes various processings. Specifically, the CPU functions as an obtaining unit 41, a positioning unit 42, a calculation unit 43, a generation unit 44, a change unit 45, and a display control unit 46 while a program stored in a storage device that is not illustrated in the drawing is executed. It should be noted that the respective numbers of the CPUs and the storage devices provided to the computer 40 may be one or more. That is, at least one processing apparatus (CPU) is connected to at least one storage device (ROM, RAM, or the like), and in a case where the at least one processing apparatus executes the program stored in the at least one storage device, the computer 40 functions as the above-described respective units. It should be noted that the processing apparatus is not limited to the CPU and may be a field-programmable gate array (FPGA) or the like.

The obtaining unit 41 obtains the output of the A/D converter 32. Specifically, the digital signal of the interfering light based on the returning light of the subject's eye of the measurement light with which the subject's eye is scanned and the reference light is obtained. Furthermore, the obtaining unit 41 performs Fourier transform on the digital signal (interfering signal) of the interfering light to obtain the tomographic image. Specifically, the obtaining unit 41 applies fast Fourier transform (FFT) to the interfering signal to obtain an OCT complex signal composed of a phase and an amplification. It should be noted that a maximum entropy method may be employed as a frequency analysis. Furthermore, the obtaining unit 41 squares an absolute value of the OCT complex signal and calculates a signal intensity (intensity) to obtain a tomographic image indicating the intensity (hereinafter, may be referred to simply as a tomographic image in some cases). This tomographic image is equivalent to an example of tomographic image data indicating a cross section of the eye fundus of the subject's eye. That is, in a case where scanning is performed plural times by using the measurement light at substantially a same position of the eye fundus of the subject's eye, the obtaining unit 41 obtains plural pieces of tomographic image data each indicating a cross section of substantially the same position of the subject. It should be noted that the plural pieces of tomographic image data are data obtained by the measurement light with which the scanning is performed at different timings. "Substantially a same position" includes an actual same position and almost same position. Ideally scanning is performed plural times at an actual same position. But in reality, scanning may be performed plural times at almost same position because of involuntary eye movement. If a tracking technique is used for tracking the eye movement, scanning may be performed plural times at almost same position because of imperfectness of the tracking technique.

It should be noted that the obtaining unit 41 also functions as a unit configured to control the X-axis scanner 53 and the Y-axis scanner 54.

The positioning unit 42 performs positioning of the plurality of tomographic images. According to the present exemplary embodiment, the positioning unit 42 performs the positioning of the plurality of tomographic images obtained by scanning substantially the same position of the eye fundus of the subject's eye plural times with the measurement light. More specifically, the positioning unit 42 performs the positioning of the plural pieces of tomographic image data to each other before the calculation unit 43 calculates a motion contrast value.

The positioning of the tomographic images can be realized by various techniques in related art. The positioning unit 42 performs the positioning of the plurality of tomographic images such that, for example, a correlation of the mutual tomographic images becomes the highest. It should be noted that the positioning is unnecessary unless the subject is a moving test body such as an eye. In addition, the positioning is unnecessary if a tracking performance is high even when the subject is the eye. That is, the positioning of the mutual tomographic images by the positioning unit 42 does not necessarily need to be performed.

The calculation unit 43 calculates a motion contrast feature quantity (hereinafter, may be referred to simply as a motion contrast value in some cases). Herein, a motion contrast refers to a contrast between tissues with a flow (for example, blood) and tissues without a flow among tissues of the subject, and a feature quantity representing this motion contrast is defined as the motion contrast feature quantity.

The motion contrast feature quantity is calculated based on a change in data between the plurality of tomographic images obtained by scanning substantially the same position plural times with the measurement light. For example, the calculation unit 43 calculates a variance of the signal intensities (luminance) of the plurality of tomographic images after the positioning is performed as the motion contrast feature quantity. More specifically, the variance of the signal intensities at the respective positions corresponding to the plurality of tomographic images after the positioning is performed is calculated as the motion contrast feature quantity. For example, since a signal intensity of an image equivalent to the blood vessel at a predetermined time is changed by a bloodstream to be different from a signal intensity of an image equivalent to the blood vessel at a time different from the predetermined time, a variance value at a part equivalent to the blood vessel is higher than a variance value at a part where a flow such as the bloodstream does not exist. That is, the motion contrast value is a value that becomes higher as the change in the subject between the plural pieces of tomographic image data is larger. Therefore, the motion contrast can be represented by generating the image based on this variance value. It should be noted that the motion contrast feature quantity is not limited to the variance value but may be any one of a standard deviation, a difference value, a decorrelation value, and a correlation value. It should be noted that the calculation unit 43 uses the variance of the signal intensities or the like but may calculate the motion contrast feature quantity by using a phase dispersion.

The calculation unit 43 also generates an averaged image by calculating an average value of the plurality of tomographic images after the positioning is performed. The averaged image is a tomographic image in which the signal intensities of the plurality of tomographic images are averaged. This averaged image may be referred to as an intensity averaged image in some cases. The calculation unit 43 compares the signal intensity of the averaged image with a threshold. In a case where the signal intensity of the predetermined position of the averaged image is lower than the threshold, the calculation unit 43 sets the motion contrast feature quantity corresponding to the predetermined position of the averaged image which is obtained based on the variance or the like as a value different from the feature quantity indicating the blood vessel. For example, in a case where the signal intensity of the averaged image is lower than the threshold, the calculation unit 43 sets the motion contrast feature quantity obtained based on the variance or the like as 0. That is, the calculation unit 43 sets the motion contrast value in a case where the representative value indicating the signal intensity is lower than the threshold as a value lower than the motion contrast value in a case where the representative value indicating the signal intensity is higher than the threshold. It should be noted that the calculation unit 43 may compare the signal intensity of the averaged image with the threshold before the variance of the signal intensities of the plurality of tomographic images is calculated as the motion contrast feature quantity. For example, in a case where the signal intensity of the averaged image is lower than the threshold, the calculation unit 43 calculates the motion contrast feature quantity as 0, and in a case where the signal intensity of the averaged image is higher than the threshold, the calculation unit 43 calculates the variance of the signal intensities of the plurality of tomographic images as the motion contrast feature quantity.

Herein, a state in which the feature quantity is 0 represents a black part in the image illustrated in FIG. 7 or the like. It should be noted that the motion contrast feature quantity may be set as a value close to 0 instead of completely 0. On the other hand, in a case where the signal intensity of the averaged image is higher than the threshold, the calculation unit 43 maintains the motion contrast feature quantity obtained based on the variance or the like. That is, the calculation unit 43 calculates the motion contrast value based on the plural pieces of tomographic image data and calculates the motion contrast value again based on the comparison result of the representative value indicating the signal intensity and the threshold.

It should be noted that the signal intensity of the averaged image (average value of the signal intensities) is used as the comparison object with the threshold, but a representative value such as a highest value, a lowest value, or a median value of the signal intensities at the positions corresponding to the plurality of tomographic images may be used. In addition, the calculation unit 43 may compare the signal intensity of one tomographic image with the threshold to control the motion contrast feature quantity instead of comparing the signal intensities obtained from the plurality of tomographic images with the threshold.

As described above, the calculation unit 43 calculates the motion contrast value based on the plural pieces of tomographic image data and a comparison result of a representative value of the plural pieces of tomographic image data indicating the signal intensity and a threshold.

The generation unit 44 generates an OCT angiography image based on the motion contrast feature quantity. The OCT angiography image is obtained by imaging the motion feature quantity calculated by the calculation unit 43. As illustrated in FIG. 7, for example, the OCT angiography image is an image in which the luminance is higher as the motion contrast feature quantity is higher, and the luminance is lower as the motion contrast feature quantity is lower. In the example of FIG. 7, a part having the high luminance is a part equivalent to the blood vessel. It should be noted that a configuration may be adopted in which the luminance is lower as the motion contrast feature quantity is higher, and the luminance is higher as the motion contrast feature quantity is lower. The OCT angiography image may be referred to as a motion contrast image or a blood vessel image in some cases. That is, the generation unit 44 generates the motion contrast image of the subject based on the motion contrast value.

In a case where the calculation unit 43 calculates the three-dimensional motion contrast feature quantity (three-dimensional data) from the three-dimensional tomographic image data, the generation unit 44 can generate the three-dimensional OCT angiography image. In addition, the generation unit 44 can generate the two-dimensional OCT angiography image projected or integrated in a depth range in an arbitrary retina direction of the three-dimensional OCT angiography image. That is, the motion contrast value in a predetermined range in the depth direction of the subject is projected or integrated in the above-described depth direction by the generation unit 44 to generate the above-described two-dimensional motion contrast image. FIG. 7 illustrates an example of the two-dimensional OCT angiography image.

Furthermore, the generation unit 44 can generate a partial three-dimensional OCT angiography image by cutting out a depth range in an arbitrary retina direction from the three-dimensional OCT angiography image. That is, the generation unit 44 generates the three-dimensional motion contrast image based on the motion contrast value in a predetermined range in the depth direction of the subject.

It should be noted that the depth range in the arbitrary retina direction can be set by an examiner (operator or technician). For example, selectable layer candidates such as a layer from inner segment/outer segment junction (IS/OS) to retinal pigment epithelium (RPE) and a layer from RPE to Bruch's membrane (BM) are displayed on a display unit 70. The examiner selects a predetermined layer from among the displayed layer candidates. Subsequently, the generation unit 44 may perform the integration in the depth direction of the retina in the layer selected by the examiner to generate the two-dimensional OCT angiography image (en-face blood vessel image) or the partial three-dimensional OCT angiography image.

In addition, the generation unit 44 may generate the OCT angiography image equivalent to the tomographic image from the motion contrast feature quantity.

Figure 8:
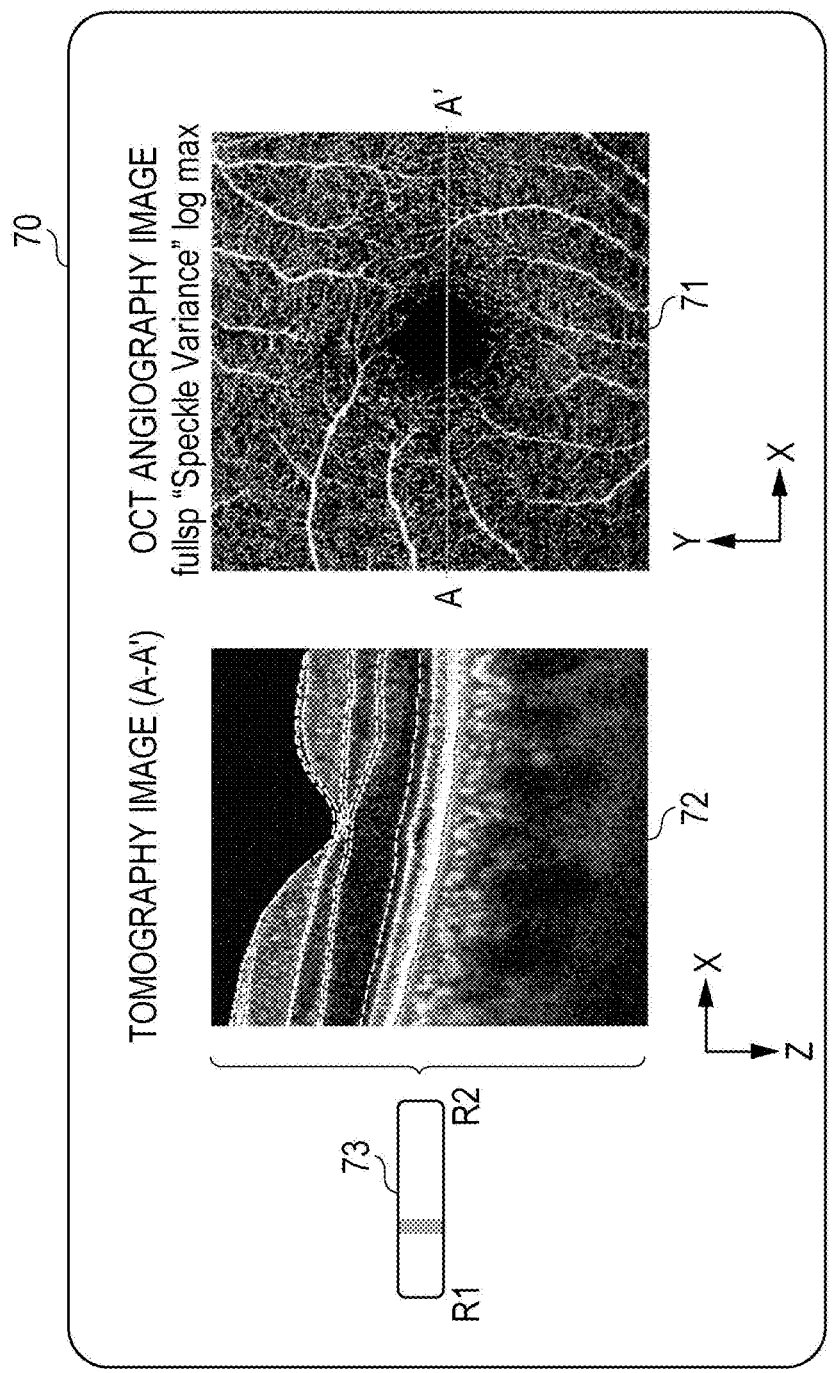
FIG. 8 illustrates an example of a display screen of a display unit according to the first exemplary embodiment.

The change unit 45 changes the threshold that is compared with the signal intensity of the averaged image. The change unit 45 accepts the change of the threshold via an arbitrary graphical user interface (GUI), for example, to perform the change of the threshold. A slide bar 73 illustrated in FIG. 8 is an example of a display (GUI) for accepting the change of the threshold. That is, the change unit 45 accepts the change of the threshold via the display for accepting the change of the threshold which is displayed on the display unit and changes the threshold.

Figure 10:
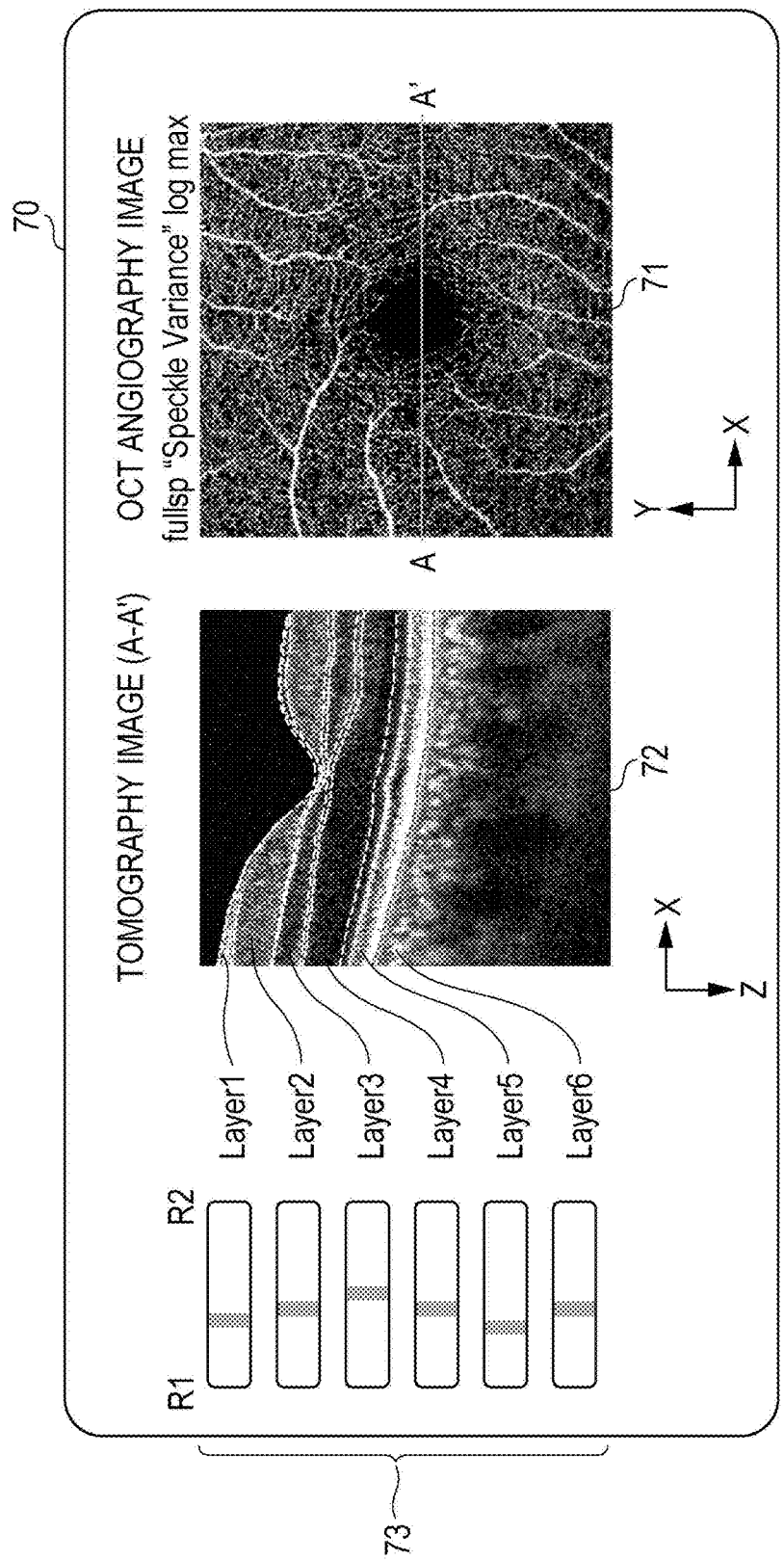
FIG. 10 illustrates an example of a display screen of the display unit according to the second exemplary embodiment.

Herein, the thresholds may be collectively changed as in an example illustrated in FIG. 8, or a GUI for accepting the change of the threshold for each layer may be provided like the slide bar 73 illustrated in FIG. 10 to perform the change of the threshold for each layer. It should be noted that the threshold may be set as a discrete value for each layer or may be set as a continuous value along the depth direction by complementing the threshold input by the examiner, for example.

In addition, the change unit 45 may automatically change the threshold. For example, the change unit 45 may change the threshold to be a different value for each layer. Specifically, by setting the threshold to be lower as the layer is deeper, the part having the low signal intensity even through the part is the blood vessel can be imaged as the blood vessel. It should be noted that the threshold may be set as a discrete value for each layer or may be set as a continuous value along the depth direction by the complementing process. It should be noted that a technique for automatically determining the threshold is not limited to a method of using the depth of the layer, and the threshold can also automatically be determined by using a value of a noise floor which will be described below, a roll-off characteristic, or the like. It should be noted that the method of setting the threshold for each layer and the like will be described in detail according to the second and subsequent exemplary embodiments.

The display control unit 46 displays various pieces of information on the display unit 70. Specifically, the display control unit 46 displays the OCT angiography image generated by the generation unit on the display unit 70. The display control unit 46 also displays a display (GUI) for accepting the change of the threshold on the display unit 70. For example, the display control unit 46 displays the slide bar 73 corresponding to an example of the GUI for accepting the change of the threshold on the display unit 70. That is, the display control unit 46 displays the motion contrast image generated by the generation unit and the display for accepting the change of the threshold on the display unit.

Furthermore, the display control unit 46 may display the tomographic image indicating the intensity on the display unit 70.

A detailed content of a specific signal processing procedure performed by the computer 40 will be illustrated in a signal processing procedure below.

The display unit 70 displays various pieces of information based on the control of the display control unit 46. The display unit 70 is, for example, a display made of liquid crystal or the like. In addition, the OCT angiography image obtained as a result of the above-described signal processing is displayed by the display unit 70.

Scanning Pattern

Next, an example scanning pattern according to the present exemplary embodiment will be described with reference to FIG. 2.

Since the temporal change of the interfering signal caused by the bloodstream is measured according to the OCT angiography, a plurality of interfering signals obtained by repeatedly measuring substantially the same position at least twice or more are needed. In FIG. 2, an axis direction of the irradiation light on the human eye 100 is set as a Z-axis (depth direction), a plane orthogonal to the Z-axis, that is, eye fundus plane directions are set as an X-axis and a Y-axis.

Figure 2:
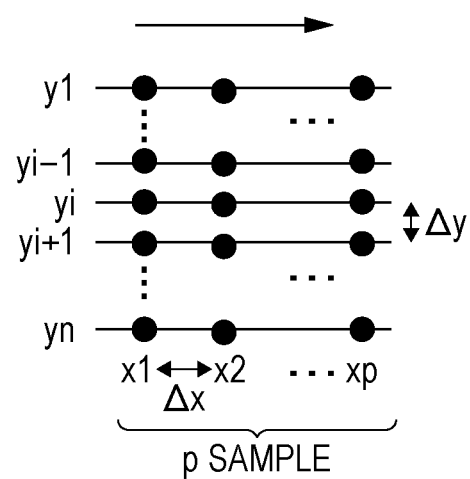
FIG. 2 illustrates an example of a scanning pattern according to the first exemplary embodiment.

In FIG. 2, positions y1 to yn represent the B scanning at mutually different Y positions, and n denotes the number of samples in a y scanning direction. Positions x1 to xp represent sample positions in an X scanning direction, and p denotes the number of samples in the X scanning direction constituting the B scanning. Interval position Δx (Δ is the uppercase Greek letter delta) denotes an interval between adjacent X positions (x pitch), and Δy denotes an interval between adjacent Y positions (y pitch). A quantity m denotes the number of measurement repetitions of the B scanning at substantially the same position. Herein, the initial position (x1, y1) can be arbitrarily set by the computer 40.

According to the present exemplary embodiment, the OCT apparatus performs a scanning method of repeating the B scanning at substantially the same position m times and moving to n pieces of y positions. It should be noted that the repetitive scanning method may be a scanning method of realizing the B scanning by repeating the A scanning at substantially the same position and then moving to the next position.

Herein, when the number of measurement repetitions m is high, the number of measurements at the same position is increased, and therefore a detection accuracy for the bloodstream is improved. On the other hand, a scanning time is lengthened, and a problem occur that a motion artifact is generated in the image by a motion of the eye during the scanning (involuntary eye movement). In addition, a problem occur that burden of an examinee is increased. According to the present exemplary embodiment, m=4 is set to carry out the scanning while a balance between the improvement in the detection accuracy and the generation of the motion artifact is taken into account. It should be noted that m may be freely changed in accordance with an A scanning speed of the OCT apparatus and a motion amount of the human eye 100. That is, the number of scanning repetitions is not limited to the above-described value.

In addition, the image sizes in x and y directions are determined by p×n. When the image sizes in the x and y directions are large, the wide range can be scanned in the case of the same measurement pitch, but the scanning time is lengthened, and the above-described problems of the motion artifact and the burden on the patient occur. According to the present exemplary embodiment, n=p=300 is set to carry out the scanning while a balance between the scanning in the wider range and the problems is taken into account. It should be noted that the above-described n and p can be appropriately freely changed. That is, the image size is not limited to the above-described value.

In addition, according to the present exemplary embodiment, the x pitch and the y pitch are determined as ½ of the beam spot diameter of the irradiation light on the eye fundus and are set as 10 micrometers (Mm). When the x pitch and the y pitch are set as ½ of the beam spot diameter on the eye fundus, it is possible to form the generated image at a high definition. If the x pitch and the y pitch are set to be smaller than ½ of the beam spot diameter on the eye fundus, there is little effect even when the resolution of the generated image is set to be even higher.

On the contrary, if the x pitch and the y pitch is set to be larger than ½ of the beam spot diameter on the eye fundus, the resolution is deteriorated, but it is possible to obtain an image in a still wider range. The x pitch and the y pitch may be freely changed in accordance with a clinical request.

As the scanning range according to the present exemplary embodiment, the x direction is set as p×Δx=3 millimeters (mm), and the y direction is set as n×Δy=3 mm.

Interfering Signal Obtaining Procedure

Next, an example of an interfering signal obtaining procedure according to the present exemplary embodiment will be described with reference to FIG. 3.

First, in step S109, the obtaining unit 41 sets an index i at a position yi in FIG. 2 as 1. Next, in step S110, the obtaining unit 41 controls a driving mechanism that is not illustrated in the drawing to move scanning positions of the X-axis scanner 53 and the Y-axis scanner 54 to (x1, yi) in FIG. 2. In step S119, the obtaining unit 41 initializes the index j of the number of measurement repetitions of the B scanning to 1.

Next, in step S120, the X-axis scanner 53, the Y-axis scanner 54 executes the j-th B scanning among the number of measurement repetitions. It should be noted that a B scanning range corresponds to (x1, yi) to (xp, yi). Herein, the wavelength-sweeping light source 10 emits light at the A scanning rate of 100 kHz, and the number of samples p in the x scanning direction constituting the B scanning is, for example, p=300. Therefore, a net B scanning time (Δtb) is represented as Expression 1.

$$\Delta tb = (1/100 \text{ kHz}) \times 300 = 3 \text{ ms} \quad (1)$$

The temporal interval of the repetitive measurements Δt is a sum of the net B scanning time Δtb and a preparation time Δtp of the X-axis scanner 53 as represented in Expression 2. The preparation time Δtp is, for example, a time for adjusting the scanning positions of the X-axis scanner 53 and the Y-axis scanner 54. When Δtp=1 millisecond (ms) is set, the following expression is established.

$$\Delta t = \Delta tb + \Delta tp = 4 \text{ ms} \quad (2)$$

Furthermore, a total measurement time tm is represented as Expression 3 by using the number of measurement repetitions m and the number of samples n in the y scanning direction.

$$tm = \Delta t \cdot m \cdot n = (\Delta tb + \Delta tp) \cdot m \cdot n \quad (3)$$

According to the present exemplary embodiment, since m=4 and y=300 are set, the total measurement time tm=3.6 s is obtained.

Herein, as the B scanning time Δtb and the temporal interval of the repetitive measurements Δt are shorter, the influence of the motion of the human eye 100 is hardly affected, and bulk motion noise is reduced. In contrast to this, when Δt is lengthy, position reproducibility is decreased by the motion of the human eye 100, and the bulk motion noise is increased. In addition, it takes longer time to perform the measurement, and the burden on the patient is increased. Herein, the bulk motion means a motion of the subject's eye, and the bulk motion noise means noise generated by the motion of the subject's eye.

Furthermore, when the temporal interval of the repetitive measurements Δt is too small, it takes shorter time to perform the bloodstream detection, and bloodstream detection sensitivity is decreased.

Thus, tm, Δt, n, p, Δtb, and Δtp are preferably selected while the above-described aspects are taken into account. It should be noted that, to increase the position reproducibility of the repetitive measurements, the X-axis scanner 53 and the Y-axis scanner 54 may perform the B scanning while the human eye 100 is tracked.

In step S130, the differential detector 31 detects the interfering light for each A scanning to be converted into the digital signal (interfering signal) via the A/D converter 32. The obtaining unit 41 obtains the interfering signal from the A/D converter 32 to be stored in a storage unit that is not illustrated in the drawing. The obtaining unit 41 obtains p pieces of A scanning signals by performing B scanning once. The p pieces of A scanning signals constitute the single B scanning signal.

In step S139, the obtaining unit 41 increments the index j of the number of measurement repetitions of the B scanning.

Next, in step S140, the obtaining unit 41 determines whether or not the index j of the number of measurement repetitions is higher than a predetermined number of measurement repetitions m. That is, the obtaining unit 41 determines whether or not the B scanning at the position yi is repeatedly performed m times. In a case where the B scanning is not repeatedly performed m times, the flow returns to S120, and the B scanning measurement at the same position is repeatedly performed. In a case where the B scanning is repeatedly performed m times, the flow proceeds to S149.

In step S149, the obtaining unit 41 increments the index i at the position yi.

Next, in step S150, the obtaining unit 41 determines whether or not the index i at the position yi is higher than the number of predetermined measurement positions n, that is, whether or not the B scanning is executed at all the n pieces of Y positions. In a case where the B scanning is not executed at all the n pieces of Y positions, the flow returns to step S110, and the measurement at the next measurement position is repeated. In a case where the B scanning is executed at all the n pieces of Y positions, the flow to the next step S160.

In step S160, the obtaining unit 41 obtains background data. The obtaining unit 41 controls a driving unit that is not illustrated in the drawing to perform the A scanning 100 times in a state in which the shutter 85 is closed (state of being inserted into the light path), and the obtaining unit 41 performs averaging of 100 A scanning signals to be stored in the storage unit. It should be noted that the number of the performances of the A scanning to obtain the background data is not limited to 100.

While the above-described steps are executed, the obtaining unit 41 obtains the plurality of interfering signals as a result of the repetitive measurements performed at substantially the same position at least twice and the background data.

Signal Processing Procedure

Next, an example of the signal processing procedure according to the present exemplary embodiment will be described with reference to FIG. 4.

Figure 4:
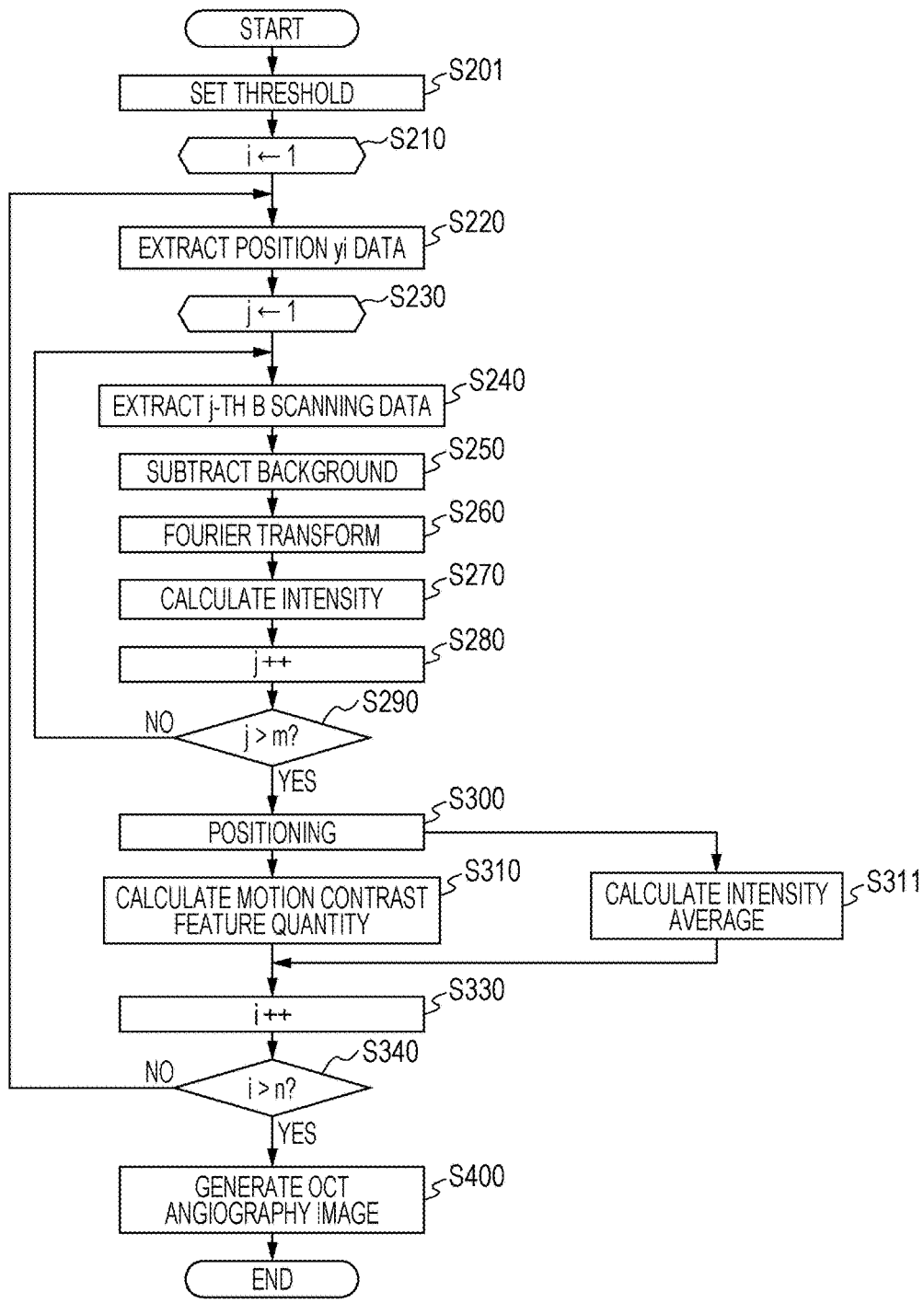
FIG. 4 is a flow chart illustrating an example of a signal processing procedure according to the first exemplary embodiment.

FIG. 4 illustrates an example flow until the obtaining unit 41 to which the interfering signal is input outputs an OCT angiography image as a result of the signal processing.

According to the present exemplary embodiment, the motion contrast feature quantity needs to be calculated to generate the OCT angiography image.

In FIG. 4, first, in step S201, the change unit 45 performs setting of a threshold to calculate a motion contrast feature quantity that will be described below. With regard to the set value of the threshold, the change unit 45 previously extracts an area where only random noise is displayed in the noise floor of the tomographic image to calculate a standard deviation σ (the Greek letter sigma), and an average intensity of the noise floors is set as +2σ. It should be noted that this threshold can be appropriately changed by the examiner.

Next, in step S210, the obtaining unit 41 sets the index i at the position yi in the y direction as 1. In step S220, the obtaining unit 41 extracts B scanning interfering signals obtained by the repetitive B scanning at the position yi (for m times) from the interfering signals obtained by the processing illustrated in FIG. 3 from the storage unit. Specifically, the plurality of B scanning interfering signals obtained by the repetitive B scanning at the position yi are read out from the storage unit.

Next, in step S230, the obtaining unit 41 sets the index j of the repetitive B scanning as 1.

In step S240, the obtaining unit 41 extracts the j-th B scanning interfering signal from the B scanning interfering signals for m times.

Figure 3:
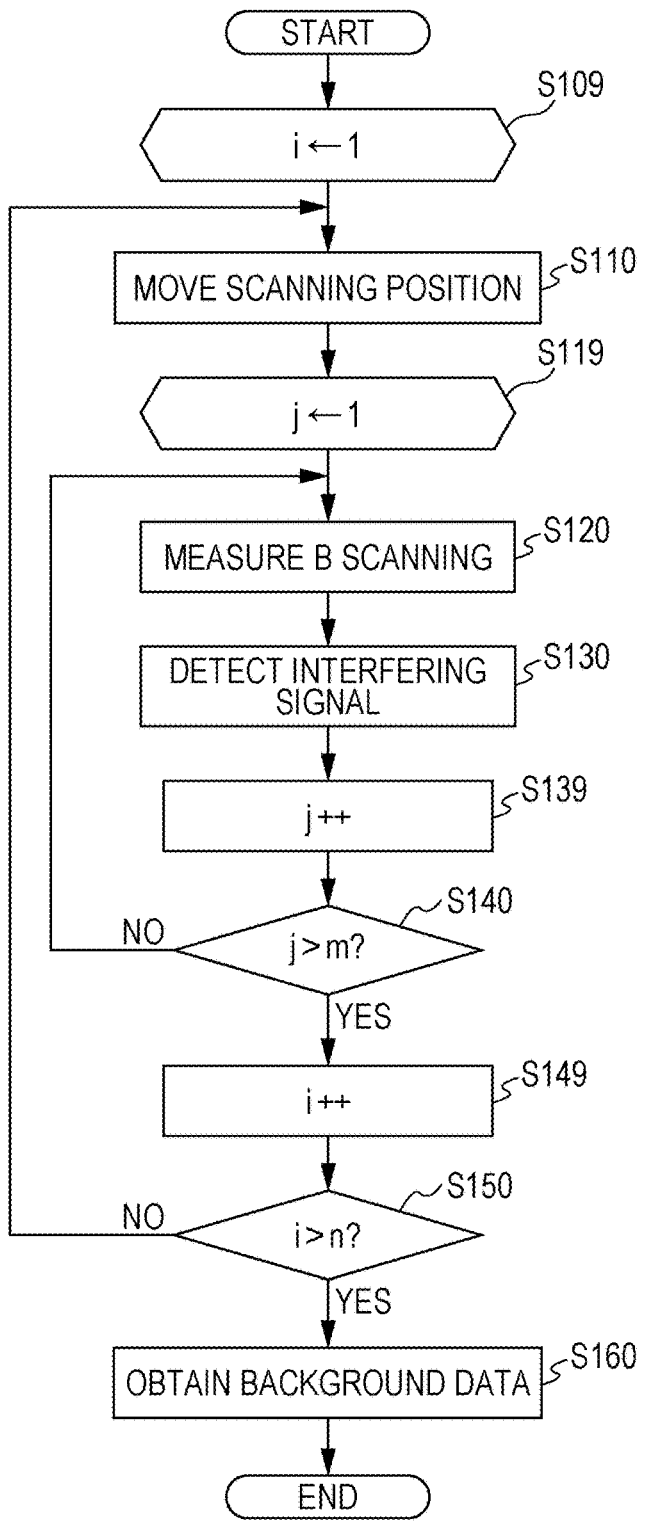
FIG. 3 is a flow chart illustrating an example of an interfering signal obtaining procedure according to the first exemplary embodiment.

Next, in step S250, the computer 40 subtracts the background data obtained in step S160 of FIG. 3 from the B scanning interfering signal obtained in step S240.

In step S260, the obtaining unit 41 performs Fourier transform of the B scanning interfering signal from which the background data is subtracted. According to the present exemplary embodiment, fast Fourier transform (FFT) is adopted.

In step S270, the obtaining unit 41 squares the absolute value of the amplitude of the B scanning interfering signal subjected to the Fourier transform in step S260. This value corresponds to an intensity of the tomographic image of the B scanning. That is, in step S270, the obtaining unit 41 obtains the tomographic image indicating the intensity.

In step S280, the obtaining unit 41 increments the number of measurement repetitions j indicating the number of repetitions of the B scanning. Subsequently, in step S290, the obtaining unit 41 determines whether or not the number of measurement repetitions j is higher than the number of measurement repetitions m. That is, the obtaining unit 41 determines whether or not the intensity calculation of the B scanning at the certain position yi is repeated m times. In a case where the number of measurement repetitions j is lower than the number of measurement repetitions m, the flow returns to step S240, and the obtaining unit 41 repeatedly performs the intensity calculation of the repetitive B scanning at the same Y position. In a case where the number of measurement repetitions j is higher than the number of measurement repetitions m, the flow proceeds to step S300.

In step S300, the positioning unit 42 performs positioning of the tomographic images for m frames of the repetitive B scanning at the certain Y position yi. Specifically, the positioning unit 42 first selects one arbitrary tomographic image from among the tomographic images for the m frames as a template. The positioning unit 42 may calculate correlations in all combinations in the tomographic images for the m frames to obtain a sum of correlation coefficients for each frame and select the tomographic image for the frame where the sum becomes the highest as the template.

Next, the positioning unit 42 collates the tomographic image selected as the template with the tomographic images for the other frames to obtain a positional shift amount ($\delta X$, $\delta Y$, $\delta \theta$) ($\delta$ is the lowercase Greek letter delta and $\theta$ is the lowercase Greek letter theta). Specifically, while a position and an angle of the template image are changed, the positioning unit 42 calculates a normalized cross-correlation (NCC) corresponding to an index representing a similarity with the tomographic images for the other frames. Subsequently, the positioning unit 42 obtains a difference of the image positions at which this value becomes the highest as the positional shift amount. It should be noted that, according to the present disclosure, the index representing the similarity can be changed in various manners as long as it is a measure representing a similarity of characteristics of the tomographic image selected as the template and the tomographic images for the other frames. For example, sum of absolute difference (SAD), sum of squared difference (SSD), zero-means normalized cross-correlation (ZNCC), phase only correlation (POC), rotation invariant phase only correlation (RIPOC), or the like may be used as the index representing the similarity.

Next, the positioning unit 42 applies the positional correction of the tomographic image indicating the intensity to the tomographic images of the (m−1) frames other than the template based on the positional shift amount ($\delta X$, $\delta Y$, $\delta \theta$) and performs the positioning of the tomographic images for the m frames. After the positioning is completed, the processings in step S310 and step S311 are performed.

In step S310, the calculation unit 43 calculates the motion contrast feature quantity. According to the present exemplary embodiment, the calculation unit 43 calculates a variance value for each pixel at the same position from the tomographic images for the m frames where the positioning is performed in step S300 and sets the variance value as the motion contrast feature quantity. It should be noted that various methods can be employed to obtain the motion contrast feature quantity, and as long as it is a measure representing a change in the luminance values of the respective pixels corresponding to the plurality of tomographic images at the same Y position, the method can be applied to the present disclosure.

On the other hand, in step S311, the calculation unit 43 calculates an average of the m tomographic images (intensity images) obtained in step S300 where the positioning is performed and generates the intensity averaged image.

In step S330, the obtaining unit 41 increments the index i at the position yi. Subsequently, in step S340, the obtaining unit 41 determines whether or not the index i is higher than the number of measurement positions n. That is, the obtaining unit 41 determines whether or not the positioning at all the n pieces of Y positions, the calculation of the intensity averaged image, and the calculation of the motion contrast feature quantity are performed. In a case where the index i is lower than the number of measurement positions n, the flow returns to S220. In a case where the index i is higher than the number of measurement positions n, the flow proceeds to step S400.

When step S340 is ended, the intensity averaged images of the respective pixels of the tomographic images (Z-X planes) at all the Y positions and three-dimensional volume data of the motion contrast feature quantity are obtained.

In step S400, the generation unit 44 generates an OCT angiography image.

A detail of step S400 will be described with reference to FIG. 5. First, processings are performed in a separate manner such that the segmentation processing of the retina layer is performed in step S401, and the threshold processing of the motion contrast feature quantity is performed in step S402.

As the segmentation processing of the retina layer in step S401, the segmentation processing using the intensity averaged image generated in step S311 will be specifically described.

The generation unit 44 extracts the intensity averaged image set as the processing target from among the intensity averaged images at the plurality of Y positions. Subsequently, the generation unit 44 respectively applies a median filter and a Sobel filter to the extracted intensity averaged image to create images (hereinafter, may be also respectively referred to as a median image and a Sobel image).

Next, the generation unit 44 creates profiles for each A scanning from the created median image and Sobel image. The created profiles are a profile of a luminance value in the median image and a profile of a gradient in the Sobel image. Subsequently, the generation unit 44 detects a peak in the profile created from the Sobel image. The generation unit 44 extracts a boundary (interface) of the respective areas of the retina layer by referring to a profile of the median image corresponding to a part in the vicinity of the peak detected from the Sobel image or a part between the peaks. That is, the generation unit 44 is equivalent to an example detection unit configured to detect the boundary of cross sections included in the subject from the tomographic image data.

FIG. 6 illustrates an example of the segmentation result. FIG. 6 illustrates an intensity averaged image at a certain Y position, and a segmentation line is overlaid as a broken line on the intensity averaged image. Six layers are detected in the segmentation processing according to the present exemplary embodiment. Components of the six layers include (1) a nerve fiber layer (NFL), (2) a layer composed of a ganglionic cell layer (GCL)+an inner plexiform layer (IPL), (3) a layer composed of an inner granular layer (INL)+an outer plexiform layer (OPL), (4) a layer composed of an outer granular layer (ONL)+an external limiting membrane (ELM), (5) a layer composed of an ellipsoid zone (EZ)+an interdigitation zone (IZ)+a retina pigment epithelium (RPE), and (6) a choroid. It should be noted that the segmentation processing described according to the present exemplary embodiment is an example, and other methods such as Dijkstra method segmentation processing using may also be employed. In addition, the number of detected layers can be arbitrarily set.

Next, a detail of the threshold processing of the motion contrast feature quantity in step S402 will be described. The calculation unit 43 performs the threshold processing of the motion contrast feature quantity based on the threshold set in step S201. Specifically, the calculation unit 43 extracts the intensity averaged image and the motion contrast feature quantity equivalent to the B scanning at a certain Y position from the intensity averaged images and the three-dimensional volume data of the motion contrast feature quantity obtained in step S340. Next, the calculation unit 43 compares the average intensity at the respective pixels in the B scanning with the threshold. In a case where the average intensity is lower than or equal to the threshold, the calculation unit 43 sets the value of the motion contrast feature quantity corresponding to the relevant pixel as 0. In a case where the average intensity is higher than the threshold, the calculation unit 43 maintains the value of the motion contrast feature quantity corresponding to the relevant pixel. While this threshold processing is repeatedly performed at all the Y positions, it is possible to obtain the three-dimensional volume data of the motion contrast feature quantity in which the influence of the intensity change caused by the random noise at a position where the blood vessel does not exist such as a position in the vicinity of the noise floor is reduced.

It should be noted that, as the value of the threshold is lower, the detection sensitivity of the motion contrast feature quantity is increased, but the noise component is also increased. On the other hand, as the value of the threshold is higher, the noise is reduced, but the sensitivity of the motion contrast detection is decreased. According to the present exemplary embodiment, the threshold is set as the average intensity of the noise floors which is +2σ (+2 standard deviation), but the threshold is not limited to this.

In step S403, the generation unit 44 generates the OCT angiography image based on the segmentation result of the retina and the threshold-processed motion contrast feature quantity. Subsequently, the display control unit 46 displays the generated OCT angiography image on the display unit 70.

Herein, an example of a generation method for the OCT angiography image will be specifically described. The generation unit 44 cuts out an area corresponding to an arbitrary layer, for example, a layer composed of the ganglionic cell layer (GCL)+the inner plexiform layer (IPL) from the three-dimensional volume data of the motion contrast feature quantity. Subsequently, the generation unit 44 determines a representative value of the motion contrast feature quantity with regard to the Z direction of each A scanning. The A scanning representative value may be any of the average value, the highest value, and the median value. When this A scanning representative value is plotted (projected) two-dimensionally (the x direction, the y direction), the OCT angiography image corresponding to the layer composed of the ganglionic cell layer (GCL)+the inner plexiform layer (IPL) is generated. It should be noted that, since the motion contrast feature quantity and the segmentation result are obtained from the same tomographic image, the motion contrast feature quantity is associated with the segmentation result. Therefore, the generation unit 44 can cut out the motion contrast feature quantity of the arbitrary layer from the three-dimensional volume data of the motion contrast feature quantity by using the association between the motion contrast feature quantity and the segmentation result.

FIG. 7 illustrates an example of the OCT angiography image generated according to the present exemplary embodiment. FIG. 7 illustrates a case where a yellow spot is measured by the OCT apparatus. According to the exemplary embodiment, the generation unit 44 cuts out the motion contrast feature quantity of the layer composed of the ganglionic cell layer (GCL)+the inner plexiform layer (IPL) from the three-dimensional volume data of the motion contrast feature quantity based on the segmentation result. Subsequently, the generation unit 44 generates the OCT angiography image by projecting or integrating the cut-out motion contrast feature quantity in the depth direction of the eye fundus. That is, the generation unit 44 generates the two-dimensional motion contrast image by projecting or integrating the motion contrast value in the depth direction of the subject based on the boundary detected by the detection unit. As illustrated in FIG. 7, a part having the high motion contrast feature quantity (white part in the image) outlines the eye fundus blood vessel.

FIG. 8 illustrates an example of a display screen of the display unit 70 according to the present exemplary embodiment. FIG. 8 illustrates an OCT angiography image 71 of a specific layer based on a result of the segmentation processing in step S401, a tomographic image 72 corresponding to a line A-A' in FIG. 8, and the slide bar 73 for setting the threshold. A selection range of the slide bar 73 is from R1 to R2. According to the present exemplary embodiment, for example, when the average intensity of the noise floors of the OCT apparatus is set as m and the standard deviation is set as σ, R1=m and R2=m+3σ may be established, but the values are not limited to those.

It should be noted that the layer constituting the OCT angiography image 71 can be selected from the above-described six layers by an operation unit that is not illustrated in the drawing. That is, the examiner selects a layer from which the motion contrast feature quantity is cut out from among the results of the segmentation processing, and the generation unit 44 generates an OCT angiography image of an arbitrary layer based on the selected layer. For example, when the examiner clicks a predetermined layer on the tomographic image 72 by using an operation unit such as a mouse, the generation unit 44 detects the clicked layer and generates the OCT angiography image 71 of the clicked layer. Subsequently, the display control unit 46 displays the OCT angiography image 71 on the display unit 70.

The examiner may also define a layer for generating the OCT angiography image 71 by clicking a plurality of boundaries displayed on the display unit 70 by using the operation unit. Each time the layer for generating the OCT angiography image 71 is changed by the examiner, the generation unit 44 generates the OCT angiography image 71, and each time the OCT angiography image 71 is generated, the display control unit 46 updates the display of the display unit 70. It should be noted that names of layers and a check box (or a radio button) may be displayed in an area different from the tomographic image 72 instead of clicking the tomographic image or the boundary. According to this configuration, the examiner may be allowed to select the layer for generating the OCT angiography image 71 by clicking the check box. In this case, the display control unit 46 displays names of a plurality of layers and a plurality of check boxes corresponding to the names of the layers on the display unit 70. Subsequently, when the examiner clicks the check box, the generation unit 44 obtains the layer corresponding to the clicked check box and generates the OCT angiography image 71. It should be noted that the specific layer selected for the OCT angiography image 71 may be one layer, or a plurality of layers may also be selected.

In addition, the display control unit 46 may display layers constituting the OCT angiography image 71 or a plurality of boundaries that define the layers on the tomographic image 72 in an emphasized manner. For example, the display control unit 46 displays the plurality of boundaries that define the layers constituting the OCT angiography image 71 more brightly than the other boundaries. In this manner, the layers constituting the OCT angiography image 71 corresponding to the frontal image of the eye fundus can be easily figured out.

It should be noted that the display control unit 46 displays the two-dimensional OCT angiography image as the OCT angiography image 71 on the display unit 70 but may display the three-dimensional OCT angiography image on the display unit 70. For example, the generation unit 44 generates the three-dimensional OCT angiography image of the layer specified by the examiner by using the three-dimensional volume data of the motion contrast feature quantity. Subsequently, the display control unit 46 displays the three-dimensional OCT angiography image on the display unit 70. It should be noted that the display control unit 46 may display the three-dimensional OCT angiography image instead of the two-dimensional OCT angiography image or may display both the OCT angiography images next to each other. In a case where the two-dimensional and three-dimensional OCT angiography images are displayed on the display unit 70, when a predetermined layer is selected by the examiner, both the OCT angiography images are updated by the generation unit 44 and the display control unit 46 in synchronization with each other.

In addition, the line A-A' of the OCT angiography image 71 can be set at an arbitrary position in the Y direction. For example, when the examiner moves the line A-A' by using the operation unit, the tomographic image 72 corresponding to the line A-A' is displayed.

With reference to FIG. 5 again, in step S404, the examiner determines whether or not the threshold is appropriate by observing the OCT angiography image displayed on the display unit 70. In a case where the examiner determines as NG (no good—the examiner determines that the threshold is not OK), the examiner changes the threshold by using the operation unit in the next step S405. Subsequently, the calculation unit 43 executes the threshold processing of the motion contrast feature quantity in step S402 again, and the generation unit 44 generates the OCT angiography image again. Each time the threshold is changed, step S402 and step S403 are repeatedly executed. That is, each time the threshold is changed by the change unit, the calculation unit 43 calculates the motion contrast value, and the generation unit 44 generates the motion contrast image each time the threshold is changed by the change unit. In addition, the display control unit 46 updates the motion contrast image displayed on the display unit each time the threshold is changed by the change unit. Since the OCT angiography image is updated each time the threshold is changed, the examiner can easily figure out the appropriate threshold.

Figure 5:
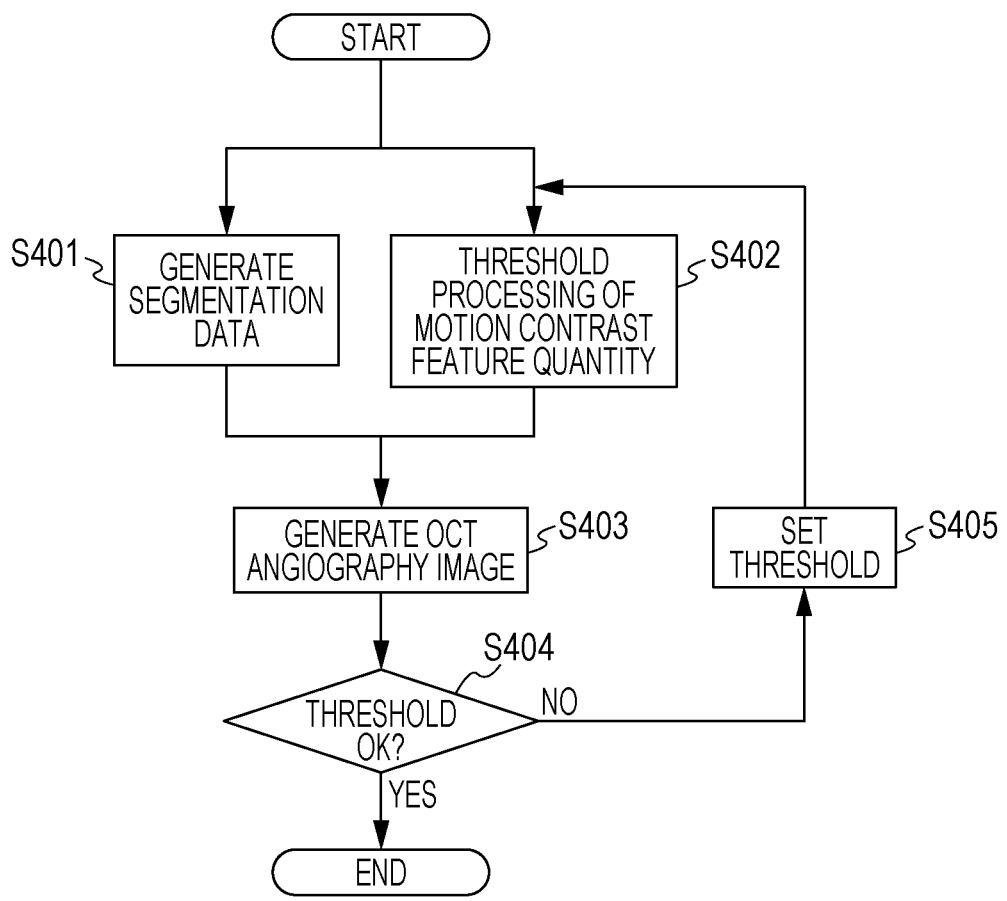
FIG. 5 is a flow chart illustrating a detail of an example of an OCT angiography image generating procedure according to the first exemplary embodiment.

When the examiner determines that the threshold is OK in step S404, the generating procedure of the OCT angiography image in step S400 of FIG. 5 is ended.

According to the above-described exemplary embodiment, since the threshold compared with the intensity of the tomographic image can be changed, the blood vessel can be imaged at a satisfactory accuracy.

It should be noted that the slide bar 73 is used for setting the threshold to be variable according to the above-described exemplary embodiment, but the configuration is not limited to this, and the apparatus may be configured such that the numeric value of the threshold can be set by using a text box, or a previously set threshold is selected by using a drop-down list.

Modified Example 1

It should be noted that the descriptions have been given of a case where the two-dimensional OCT angiography image is generated based on the detection result of the layer structure in step S401 according to the above-described exemplary embodiment, but the configuration is not limited to this, and the detection of the layer structure may be avoided. That is, in step S403, the OCT angiography image may be generated from data in an arbitrary range specified by the examiner of the three-dimensional volume data of the motion contrast feature quantity. That is, step S401 is not requisite processing.

Figure 13:
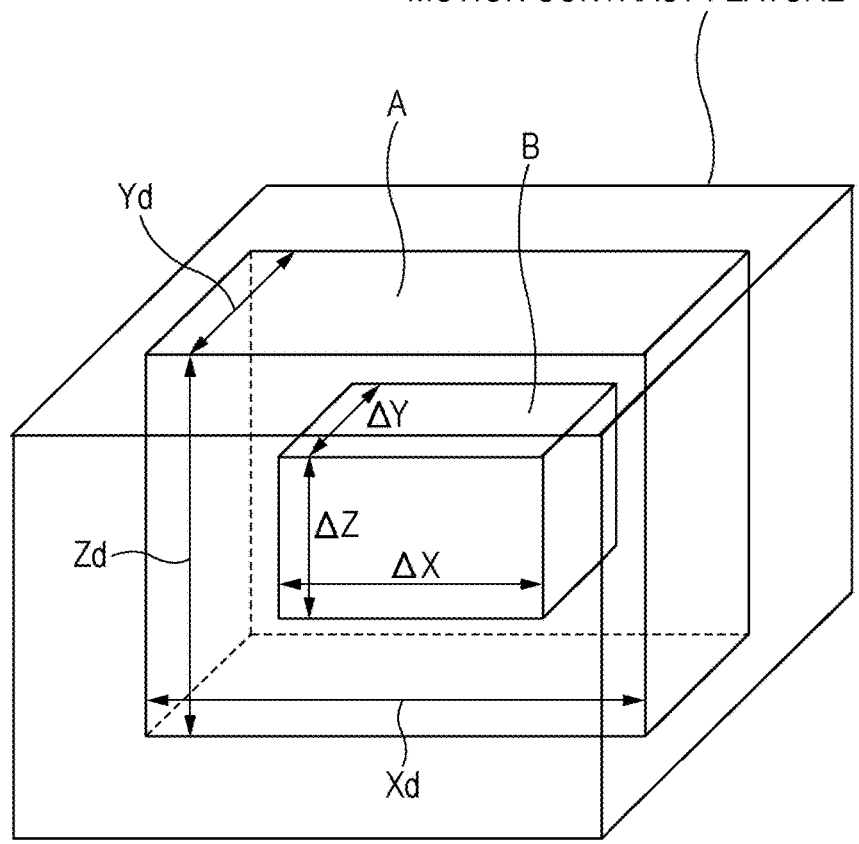
FIG. 13 illustrates an example of three-dimensional volume data according to a motion contrast feature quantity.

FIG. 13 illustrates the three-dimensional volume data of the motion contrast feature quantity. Furthermore, an area A represents a range (Xd, Yd, Zd) wished to be displayed on the display unit 70. This range is input by the examiner via, for example, a GUI. For example, the examiner inputs coordinates of the range wished to be displayed on the display unit 70. The generation unit 44 extracts the motion contrast feature quantity of the range (Xd, Yd, Zd) input by the examiner from the three-dimensional volume data of the motion contrast feature quantity and generates the OCT angiography image. The OCT angiography image generated by the generation unit 44 may be the two-dimensional OCT angiography image projected or integrated in the depth direction Z or the three-dimensional OCT angiography image.

Second Exemplary Embodiment

According to a second exemplary embodiment, a different mode from the first exemplary embodiment will be described with regard to the setting of the threshold.

The second exemplary embodiment is characterized in that the threshold is changed for each layer by using the segmentation result of the retina layer in step S400 of FIG. 4. When a state in which the blood vessel density varies for each retina layer in the depth direction because of the structure of the retina of the human eye is taken into account, the threshold is preferably set to be variable for detecting the blood vessel for each layer.

Figure 9:
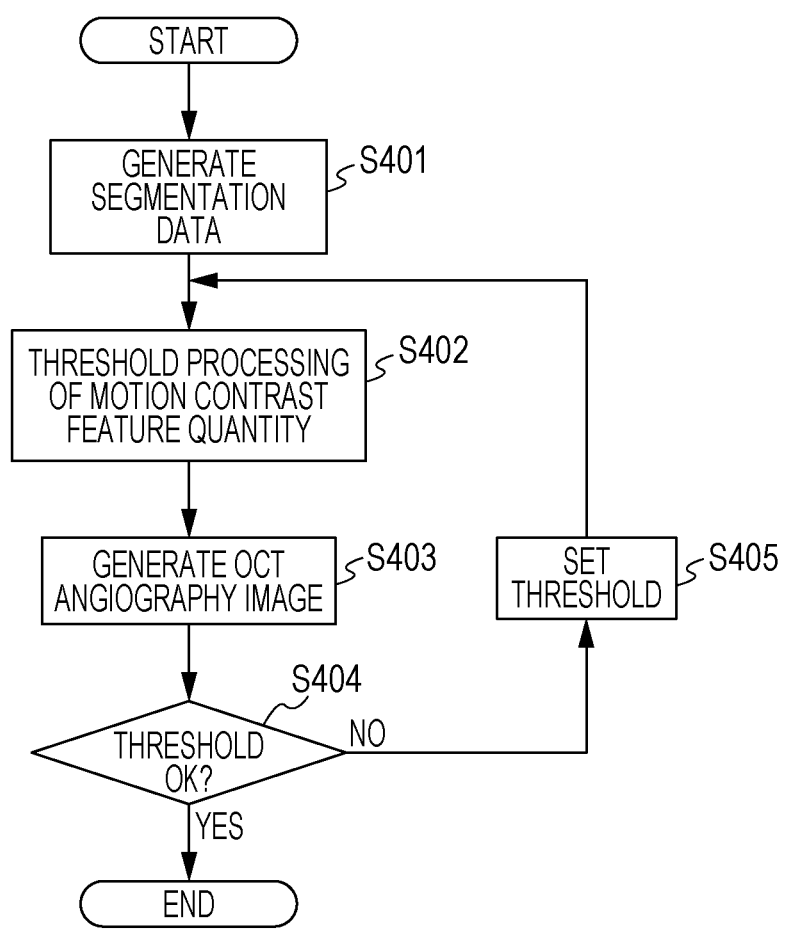
FIG. 9 is a flow chart illustrating a detail of an example of the OCT angiography image generating procedure according to a second exemplary embodiment.

FIG. 9 illustrates a flow of a processing procedure of the OCT angiography image generation according to the present exemplary embodiment. A difference from the first exemplary embodiment of FIG. 5 resides in that the threshold processing of the motion contrast feature quantity in step S402 is executed after the segmentation data is generated, that is, after step S401.

In step S402, the calculation unit 43 performs the threshold processing on the intensity averaged image and the three-dimensional volume data of the motion contrast feature quantity obtained in step S340 for each layer detected in the segmentation. Specifically, the calculation unit 43 obtains the intensity averaged image and the motion contrast feature quantity equivalent of the B scanning at a certain Y position from the memory. Subsequently, with respect to the threshold set for each layer, in a case where the average intensity at the respective pixels (positions) in the B scanning is lower than or equal to the threshold, the calculation unit 43 sets the value of the motion contrast feature quantity corresponding to the relevant pixel as 0. It should be noted that the motion contrast feature quantity may be set as a value close to 0 instead of being set as completely 0. In a case where the average intensity is higher than the threshold, the calculation unit 43 maintains the value of the motion contrast feature quantity corresponding to the relevant pixel.

Herein, with regard to the setting of the threshold, the threshold may be set to be variable by the slide bar 73 for each of the plurality of layers with respect to the tomographic image 72 displayed on the display unit 70. FIG. 10 illustrates an example of the display unit 70 according to the second exemplary embodiment. When a GUI for accepting the change of the threshold for each layer is provided like the slide bar 73 illustrated in FIG. 10, for example, it is possible to set the thresholds of six layers from Layer 1 to Layer 6. Herein, components of the six layers are equivalent to the above-described layers as follows.

Layer 1: (1) Nerve fiber layer (NFL)
Layer 2: (2) Ganglionic cell layer (GCL)+inner plexiform layer (IPL)
Layer 3: (3) Inner granular layer (INL)+outer plexiform layer (OPL)
Layer 4: (4) Outer granular layer (ONL)+external limiting membrane (ELM)
Layer 5: (5) Ellipsoid zone (EZ)+interdigitation zone (IZ)+retina pigment epithelium (RPE)
Layer 6: (6) Choroid It should be noted that the change unit 45 accepts the change of the threshold via the slide bar 73 and performs the change of the threshold. That is, the change unit 45 changes the threshold for each layer included in the subject. Herein, the slide bar 73 illustrated in FIG. 10 is an example of the GUI for accepting the change of the threshold. It should be noted that the classifications of the layers are not limited to the above-described six types.

According to the above-described exemplary embodiment, since the threshold compared with the intensity of the tomographic image can be changed, it is possible to perform the imaging of the blood vessel at a satisfactory accuracy. For example, because of the structure of the eye, an area (layer) where a blood vessel density is coarse and an area where the blood vessel density is dense exist depending on the depth direction. In particular, it is necessary to suppress false extraction of the blood vessel caused by the influence of the noise in the area where the blood vessel density is coarse. In the above-described situation too, according to the above-described exemplary embodiment, since the threshold can be set for each layer, it is possible to perform the imaging of the blood vessel at a satisfactory accuracy in accordance with the characteristics of the layers.

The threshold is changed by the examiner via the GUI according to the above-described exemplary embodiment, but the threshold may automatically take a different value for each layer. For example, in a case where the blood vessel density is previously figured out for each layer, the threshold may automatically take a different value for each layer. That is, the change unit 45 can automatically set an initial value of the threshold for each layer based on information of the blood vessel density for each layer. That is, a plurality of values are set as the thresholds in accordance with the layers included in the subject. It should be noted information in which the position of the layer or the name is associated with the threshold is previously stored in the memory, and the change unit 45 may automatically set the initial value of the threshold for each layer based on the association information stored in the memory.

It should be noted that the threshold may be set as a discrete value for each layer or may be set as a continuous value along the depth direction by complementing or the like.

Modified Example 2

According to the above-described second exemplary embodiment, the mode has been described in which the threshold is changed for each layer while the blood vessel density in the depth direction is taken into account, but the threshold may be changed in accordance with the blood vessel density not only in the Z direction but also in the X and Y directions.

For example, the area where the blood vessel density is low exists on the XY plane too as represented by the avascular zone (FAZ—Foveal Avascular Zone) in the yellow spot illustrated in the OCT angiography image 71 of FIG. 10. The display control unit 46 may divide, for example, the XY plane into a lattice pattern and display a GUI with which the threshold can be set for each area on the display unit 70. Subsequently, the change unit 45 accepts the change of the threshold by the examiner via the GUI and performs the change of the threshold in each area of the XY plane. With this configuration, since the threshold can be set more finely set, it is possible to perform the imaging of the blood vessel at a still higher accuracy.

When an area B ($\Delta X$, $\Delta Y$, $\Delta Z$) in FIG. 13 is an area where the blood vessel density is low, the examiner may set the area ($\Delta X$, $\Delta Y$, $\Delta Z$) via the GUI and increase the threshold in the area more than the other areas to suppress the false extraction of the blood vessel caused by the noise. It should be noted that the area where the blood vessel density is low may be set by using $\Delta X$ and $\Delta Y$ in the two-dimensional area, and the threshold may be increased in the area more than the other areas to suppress the false extraction of the blood vessel. The threshold in the area B selected by the examiner can be changed by the slide bar 73 or the like.

According to the above-described exemplary embodiment, since the range for changing the threshold can be selected without the limitation caused by the boundary, it is possible to improve the operability of the examiner.

In addition, according to the above-described exemplary embodiment, since the threshold can be set more finely, it is possible to perform the imaging of the blood vessel at a still higher accuracy.

Third Exemplary Embodiment

Figure 11:
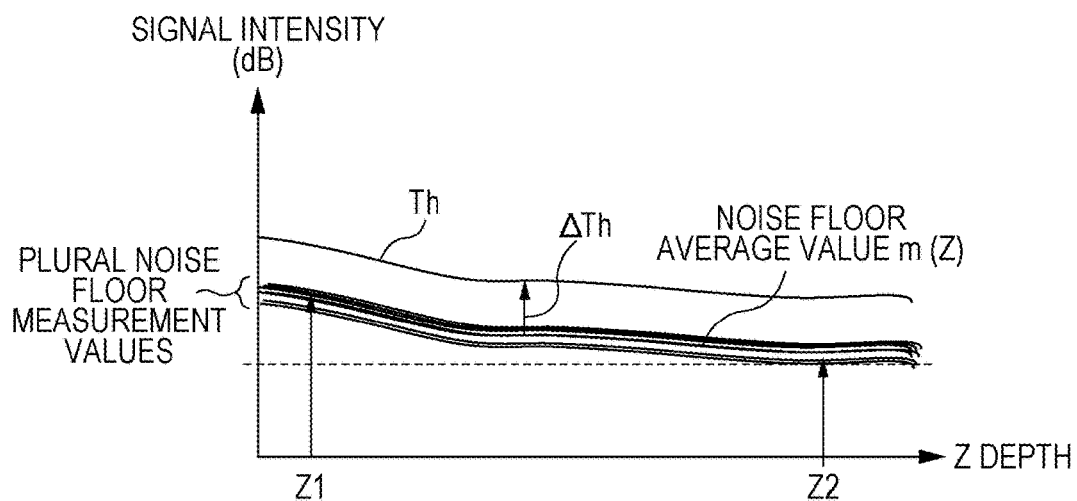
FIG. 11 illustrates an example of a Z direction dependency of a noise characteristic of an OCT apparatus according to a third exemplary embodiment.

According to the exemplary embodiments described thus far, it is assumed that the intensity of the noise floor does not change in the depth direction of the OCT tomographic image. However, the noise characteristics of high frequency components and low frequency components may differ from each other in a case where an actual interfering signal is measured. This means that, when the signal intensity is obtained by performing the Fourier transform on the interfering signal, the intensity distribution of the noise floor varies in the depth direction. FIG. 11 illustrates an example of the signal intensity of the noise floor. A difference of the signal intensity of the noise floor exists in a shallow position (Z1) and a deep position (Z2) in terms of the depth, and it is non-negligible in some cases if the threshold compared with the signal intensity of the tomographic image data is set as a fixed value.

It is characterized in a third exemplary embodiment that the threshold is automatically determined from the characteristic of the noise floor for each depth in a case where the intensity of the noise floor has dependency in the depth direction as described above.

Specifically, the change unit 45 may determine the threshold based on a distribution of the signal intensities obtained from the signal intensities of the noise floors (noise distribution) measured plural times as illustrated in FIG. 11. For example, the change unit 45 calculates an average value m(Z) by performing averaging of the signal intensities of the plurality of noise floors for each depth. Subsequently, the change unit 45 determines a value that is higher than the average value m(Z) by a predetermined value (ΔTh) as the threshold Th. That is, the change unit 45 changes the threshold in accordance with the depth of the layer included in the subject. More specifically, the change unit 45 changes the threshold based on the noise distribution in the depth direction of the subject. From a different perspective, the threshold is changed in accordance with the depth position of the subject.

It should be noted that the threshold Th is determined by using the average value of the signal intensities of the noise floors measured plural times, but the configuration is not limited to this. The median value, the highest value, or the lowest value of the signal intensities of the noise floors measured plural times may also be used. In addition, the measurement of the signal intensity of the noise floor may be performed once instead of the plural times. It should be noted that the obtaining unit 41 obtains the interfering signal generated in a state in which the shutter 85 is closed as an intensity signal of the noise floor.

According to the above-described exemplary embodiment, since the threshold can be automatically set while the change in the depth direction of the noise floor is taken into account, it is possible to perform the imaging of the blood vessel at a satisfactory accuracy. More specifically, the noise characteristic on the OCT apparatus is not necessarily constant in the Z direction. At this time, with the setting of the same threshold, the extraction accuracy of the blood vessel is more deteriorated at the depth position where the noise characteristic is more degraded. In this manner, the outline accuracy of the blood vessel may be decreased in some cases because of a problem on the apparatus in the depth direction of the OCT tomographic image. In the above-described situation too, according to the above-described exemplary embodiment, since the threshold is determined while the change in the depth direction of the noise floor is taken into account, it is possible to perform the imaging of the blood vessel at a satisfactory accuracy.

It should be noted that the threshold automatically determined based on the noise characteristic can be changed by the slide bar 73 illustrated in FIG. 10 or the like.

Fourth Exemplary Embodiment

A fourth exemplary embodiment relates to a mode in which the threshold is determined based on the roll-off characteristic derived from the OCT apparatus side.

The roll-off characteristic in the OCT apparatus system is a characteristic in which the signal intensity is more decreased as the position is deeper along the depth direction of the retina. For example, the signal intensity is decreased by 5 dB when the depth is at 1 mm.

Figure 12:
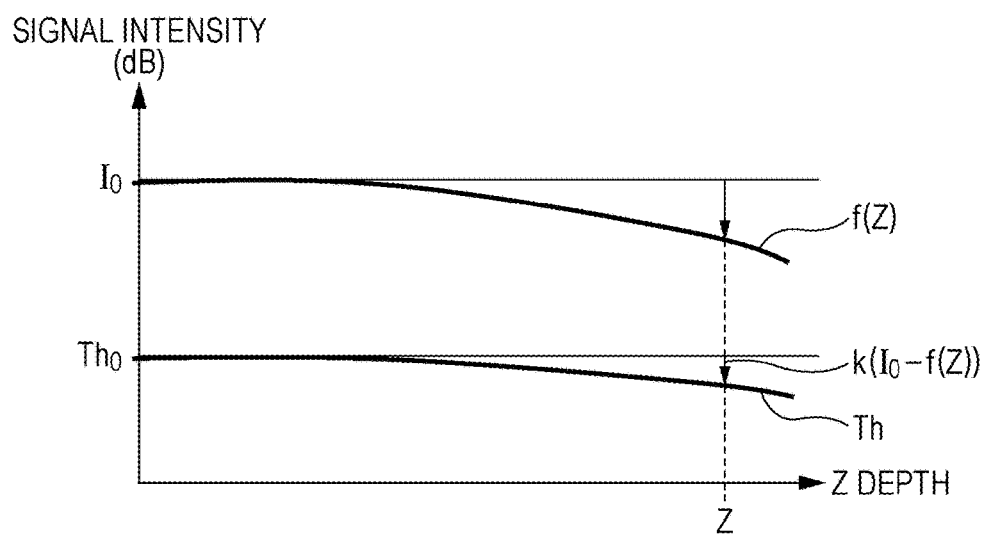
FIG. 12 illustrates an example of a roll-off characteristic of the OCT apparatus according to a fourth exemplary embodiment.

FIG. 12 illustrates an example of the roll-off characteristic of the OCT apparatus. The obtaining unit 41 can obtain the roll-off characteristic from the interfering signal. In FIG. 12, the roll-off characteristic is represented as a function f(z). When the signal intensity at Z=0 is set as $I_0$, the change unit 45 can automatically set the threshold Th at the depth Z as in Expression 4 while the roll-off characteristic f(z) is taken into account. That is, the change unit 45 changes the threshold based on the change in the signal intensity of the tomographic image data in the depth direction of the subject.

$$Th(z)=Th_0-k(I_0-f(Z)) \qquad (4)$$

Where this coefficient k is, for example, a coefficient that can be arbitrarily set as a real number from 0 to 1. In Expression 3, when the value of the coefficient k is increased, the threshold is decreased, and the effect of further increasing the detection sensitivity of the motion contrast feature quantity is expected, but the value of the coefficient k may be set while the influence of the noise is also taken into account. It should be noted that the coefficient k may be changed by the GUI such as the slide bar 73. In addition, the change unit 45 may automatically determine the coefficient k in accordance with the blood vessel density according to the second exemplary embodiment. For example, the change unit 45 sets the coefficient k to be lower as the blood vessel density is higher. In addition, the change unit 45 may automatically determine the coefficient k in accordance with the noise characteristic according to the third exemplary embodiment. That is, the coefficient k is increased as the position is deeper along the depth direction of the retina.

According to the above-described exemplary embodiment, since the threshold can be automatically set while the roll-off characteristic is taken into account, it is possible to perform the imaging of the blood vessel at a satisfactory accuracy. More specifically, when the threshold is set as one fixed value irrespective of the presence of the roll-off characteristic, the extraction accuracy of the blood vessel is more deteriorated as the position is deeper where the signal intensity is more decreased. In the above-described situation too, according to the above-described exemplary embodiment, since the threshold is determined while the roll-off characteristic is taken into account, it is possible to perform the imaging of the blood vessel at a satisfactory accuracy.

It should be noted that the threshold automatically determined based on the roll-off characteristic can be changed by the slide bar 73 illustrated in FIG. 10 or the like.

In addition, according to the above-described exemplary embodiment, the signal intensity $I_0$ at Z=0 is used as the reference, but the signal intensity at the position at Z=0 does not necessarily need to be adopted.

For example, the signal intensity at Z=0 is a DC component of the interfering signal, and the signal intensity is not stably obtained in some cases since the DC component remains as noise. Therefore, intensity data in the vicinity of Z=0 may be obtained and extrapolated to determine the intensity $I_0$ at Z=0.

It should be noted that the roll-off characteristic of the OCT apparatus is obtained by measuring the interfering signal while a reflection mirror is installed instead of the subject and shifted from a coherence gate position in the Z direction. At this time, since auto-correlation components remain as noise at the position at Z=0 (coherence gate position), the interfering signal data from a position slightly deeper than Z=0 (for example, approximately 150 um) is obtained in general. Therefore, the intensity $I_0$ at Z=0 is preferably determined while several pieces of intensity data at positions slightly deeper than Z=0 are obtained and extrapolated.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-094342, filed May 1, 2015, which is hereby incorporated by reference herein in its entirety.

What is claimed is:

1. An image generating apparatus comprising:
one or more processors; and
memory storing instructions that, when executed by the one or more processors, cause the image generating apparatus to function as:
an obtaining unit configured to obtain plural pieces of tomographic image data, wherein each piece of tomographic image data indicates a cross section of substantially the same position of a subject,
a change unit configured to set a threshold value of a threshold,
a calculation unit configured to calculate a motion contrast value based on the plural pieces of tomographic image data and a result of comparing the threshold value and a representative value of the plural pieces of tomographic image data indicating a signal intensity, and;
a generation unit configured to generate a motion contrast image of the subject based on the calculated motion contrast value,
wherein, in response to a user operation received from a user via a user interface, the change unit changes the threshold value based on the user operation such that the generated motion contrast image of the subject changes based on the changed threshold value.

2. The image generating apparatus according to claim 1, wherein the image generating apparatus further functions as a display control unit configured to display, to the user, the motion contrast image generated by the generation unit and a display image for accepting a change of the threshold value on a display,
wherein the change unit accepts the change of the threshold value via the display image for accepting the change of the threshold value which is displayed on the display and changes the threshold value,
wherein the calculation unit calculates the motion contrast value each time the change unit changes the threshold value,
wherein the generation unit generates the motion contrast image each time the change unit changes the threshold value, and
wherein the display control unit updates the motion contrast image displayed on the display the each time the change unit changes the threshold value.

3. The image generating apparatus according to claim 1, wherein the calculation unit calculates the motion contrast value based on the plural pieces of tomographic image data and recalculates the motion contrast value based on the result of comparing the threshold value and the representative value.

4. The image generating apparatus according to claim 1, wherein the motion contrast value is a value that becomes higher as a change in the subject between the plural pieces of tomographic image data is larger, and
wherein the calculation unit sets the motion contrast value in a case where the representative value indicating the signal intensity is lower than the threshold value to be lower than the motion contrast value in a case where the representative value indicating the signal intensity is higher than the threshold value.

5. The image generating apparatus according to claim 1, wherein the change unit changes the threshold value for each layer included in the subject.

6. An image generating apparatus comprising:
one or more processors; and
memory storing instructions that, when executed by the one or more processors, cause the image generating apparatus to function as:
an obtaining unit configured to obtain plural pieces of tomographic image data, wherein each piece of tomographic image data indicates a cross section of substantially the same position of a subject,
a calculation unit configured to calculate (1) a first motion contrast value in a first position based on the plural pieces of tomographic image data and a result of comparing a first threshold value and a representative value of the plural pieces of tomographic image data indicating a signal intensity in the first position, and to calculate (2) a second motion contrast value in a second position, located deeper than the first position, based on the plural pieces of tomographic image data and a result of comparing a second threshold value, different from the first threshold value, and a representative value of the plural pieces of tomographic image data indicating a signal intensity in the second position; and
a generation unit configured to generate a motion contrast image of the subject,
wherein the generation unit generates the motion contrast image of the subject based on the first and second motion contrast values.

7. The image generating apparatus according to claim 6, wherein the second threshold value is lower than the first threshold value.

8. The image generating apparatus according to claim 1, wherein the motion contrast value is three-dimensional data, and
wherein the generation unit generates the motion contrast image two-dimensionally by projecting or integrating the motion contrast value in a predetermined range in a depth direction of the subject in the depth direction.

9. The image generating apparatus according to claim 1, wherein the motion contrast value is three-dimensional data, and
wherein the generation unit generates the motion contrast image three-dimensionally based on the motion contrast value in a predetermined range in a depth direction of the subject.

10. The image generating apparatus according to claim 1, wherein the motion contrast value is three-dimensional data,
wherein the image generating apparatus further functions as a detection unit configured to detect a boundary of layers included in the subject from the tomographic image data, and
wherein the generation unit generates the motion contrast image two-dimensionally by projecting or integrating the motion contrast value in a depth direction of the subject based on the boundary detected by the detection unit.

11. The image generating apparatus according to claim 1, wherein the representative value is an average value of the signal intensities of the plural pieces of tomographic image data.

12. The image generating apparatus according to claim 1, wherein the motion contrast value is one of the following: a variance value, a decorrelation value, and a difference value between the plural pieces of tomographic image data.

13. The image generating apparatus according to claim 11, wherein the image generating apparatus further functions as a positioning unit configured to performing positioning of the plural pieces of tomographic image data with each other before the motion contrast value is calculated.

14. The image generating apparatus according to claim 1, wherein the subject is an eye fundus and the plural pieces of tomographic image data indicate a cross section of the eye fundus of an eye of a person.

15. A method for an image generating apparatus, the method comprising:
obtaining plural pieces of tomographic image data, wherein each piece of tomographic image data indicates a cross section of substantially the same position of a subject;
setting a threshold value of a threshold;
calculating a motion contrast value based on the plural pieces of tomographic image data and a result of comparing the threshold value and a representative value of the plural pieces of tomographic image data indicating a signal intensity; and
generating a motion contrast image of the subject based on the calculated motion contrast value,
wherein, in response to a user operation received from a user via a user interface, setting includes changing the threshold value based on the user operation such that the generated motion contrast image of the subject changes based on the changed threshold value.

16. A non-transitory computer-readable storage medium storing a program causing a computer to perform the method according to claim 15.

17. The image generating apparatus according to claim 1, wherein the threshold is configured to be utilized to distinguish those features of the subject that have a quality and those features of the subject that do not have the quality.

18. The image generating apparatus according to claim 17, wherein the threshold value is a first threshold value based on a noise value, the change to the first threshold value results in a second threshold value that is different from the first threshold value, the quality is flow, the features are tissues, and the second threshold value is configured to be utilized to distinguish tissues having a flow and tissues not having a flow among tissues of the subject.

* * * * *